US005658754A

United States Patent [19]
Kawasaki

[11] Patent Number: 5,658,754
[45] Date of Patent: Aug. 19, 1997

[54] CELL-FREE SYNTHESIS AND ISOLATION OF NOVEL GENES AND POLYPEPTIDES

[75] Inventor: Glenn H. Kawasaki, Seattle, Wash.

[73] Assignee: Optein, Inc., Seattle, Wash.

[21] Appl. No.: 798,985

[22] Filed: Nov. 29, 1991

Related U.S. Application Data

[63] Continuation of Ser. No. 417,357, Oct. 5, 1989, abandoned.
[51] Int. Cl.$^6$ .............................. C12P 21/02; C12N 15/00
[52] U.S. Cl. .................. 435/69.1; 435/68.1; 435/69.2; 435/69.3; 435/69.4; 435/69.5; 435/69.6; 435/172.3; 435/172.1; 435/3; 435/4; 435/10; 435/17
[58] Field of Search .................... 435/68.1, 69.1, 435/69.2, 69.3, 69.4, 69.5, 69.6, 172.3, 172.1; 938/3, 4, 10, 11, 12, 13, 14, 15, 16, 19, 21, 44

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,710,464 | 12/1987 | Belagaje et al. | 435/172.3 |
| 4,800,159 | 1/1989 | Mullis et al. | 435/172.3 |

FOREIGN PATENT DOCUMENTS

2183661  6/1987  United Kingdom.

OTHER PUBLICATIONS

Williams et al., *Ann. Rev. Immunol.*, 6:381–405 (1988).
Williams, *Science*, 243:1564–1570 (1989).
Tuerk et al., *Science*, 249:505–510 (1990).
Abelson, *Science*, 249:488–489 (1990).
Fields and Song, "A Novel Genetic System to Detect Protein–Protein Interactions," *Nature* 340:245–246, 1989.
Paul M. Lizardi et al., "Exponential Amplification of Recombinant–RNA Hybridization Probes," *Bio/Technology* 6:1197–1202, Oct. 1988.
Alan R. Kimmel, "Guide To Molecular Cloning Techniques," *Methods of Enzymology* 152:248–253, 1987.
Krawetz et al., "In vitro translation of elastin mRNA and processing of the translated products and the signal sequence of elastin a," *Can. J. Biochem. Cell. Biol.* 61:274–286, 1983.
Merrick, "Translation of Exogenous mRNAs in Reticulocyte Lysates," *Meth Enzymol.* 101:38, 1983.
Kozak, "An analysis of 5'-noncoding sequences from 699 vertebrate messenger RNAs," *Nucleic Acids Res.* 15:8125–8148, 1987.
Jobling et al., "In vitro transcription and translational efficiency of chimeric SP6 messenger RNAs devoid of 5' vector nucleotides," *Nucleic Acids Res.* 16:4483–4498, 1988.
Jobling and Gehrke, "Enhanced translation of chimaeric messenger RNAs containing a plant viral untranslated leader sequence," *Nature* 325:622–625, 1987.
Hopp et al., *Bio/Technology* 6:1204–1210, 1988.

Haruna and Spiegleman, "Specific Template Requirements of RNA Replicases*," *Proc. Nat. Acad. Sci.* 54:579–587, 1965.
Lim and Sauer, "Alternative packing arrangements in the hydrophobic core of π repressor," *Nature* 339:31–36, 1989.
Burke and Mogg, "Construction of a vector, pRSV$_{cat}$amb38, for the rapid and sensitive assay of amber suppression in human and other mammalian cells", *Nucleic Acids Res.* 13:1317–1326, 1985.
Capone et al. "Amber, ochre and opal suppressor tRNA genes derived from a human serine tRNA gene," *EMBO J.* 4:213–221, 1985.
Diamond et al., "Structure and Properties of a Bovine Liver UGA Suppressor Serine tRNA with a Tryptophan Anticodon," *Cell* 25:497–506, 1981.
Hudziak et al., "Establishment of Mammalian Cell Lines Containing Multiple Nonsense Mutations and Functional Suppressor tRNA Genes," *Cell* 31:137–146, 1982.
Laski et al., "Synthesis of an ochre suppressor tRNA gene and expression in mammalian cells," *EMBO J.* 3:2445–2452, 1984.
Capecchi et al., "Yeast Super–Suppressors Are Altered tRNAs Capable of Translating a Nonsense Codon in vitro", *Cell* 6:269–277, 1975.
Gesteland et al., "Yeast Suppressors of UAA and UAG Nonsense Codons Work Efficiently in vitro via tRNA," *Cell* 7:381–390, 1976.
Pelham, "Leaky UAG termination codon in tobacco mosaic virus RNA," *Nature* 272:469–471, 1978.
Krieg and Melton, "Functional messenger RNAs are produced by SP6 in vitro transcription of cloned cDNAs," *Nucleic Acids Res.* 10:7057–7070, 1984.
H.A. Erlich (ed.), PCR Technoloqy, Stockton Press, New York. N.Y., 1989.
H.A. Erlich (ed.), *Polymerase Chain Reaction: Current Communications in Molecular Biology*, Cold Spring Harbor Press, Cold Spring Harbor, N.Y., 1989.
Pluskal et al., *BioTechniques* 4:272–283, 1986.
Lynch, "Use of Antibodies to Obtain Specific Polysomes", *Methods of Enzymology*, (eds. Berger and Kimmel, in Guide to Molecular Cloning Techniques) 152:248–252 (1987).
Korman et al., *Proc. Natl. Acad. Sci. USA* 79: 1844–1848 (1982).
Jackson et al., *Methods in Enzymology*, 96:50–74 Academic press, New York (1983).

*Primary Examiner*—Robert A. Wax
*Attorney, Agent, or Firm*—Townsend and Townsend and Crew LLP

[57] ABSTRACT

A method for the cell-free synthesis and isolation of novel genes and polypeptides is provided. Within one embodiment, an expression unit is constructed onto which semi-random nucleotide sequences are attached. The semi-random nucleotide sequences are first transcribed to produce RNA, and then translated under conditions such that polysomes are produced. Polysomes which bind to a substance of interest are then isolated and disrupted; and the released mRNA is recovered. The mRNA is used to construct cDNA which is expressed to produce novel polypeptides.

50 Claims, No Drawings

CELL-FREE SYNTHESIS AND ISOLATION OF NOVEL GENES AND POLYPEPTIDES

This is a Continuation of application Ser. No. 07/417,357, filed Oct. 5, 1989, now abandoned.

TECHNICAL FIELD

The present invention generally relates to the synthesis and isolation of novel genes and polypeptides in vitro and, more specifically, to methods of generating and expressing semi-random DNA or RNA sequences, isolating novel genes from those sequences, and using those genes to create novel polypeptides.

BACKGROUND OF THE INVENTION

The isolation of novel genes and polypeptides from semi-random sequences is currently limited by the need to screen a large, genetically diverse population of cells in order to obtain the sequence(s) of interest. For example, a polypeptide string of 10 amino acids has $20^{10}$ or approximately $10^{13}$ possible permutations. If 10 of these permutations had a desirable characteristic (such as the ability to bind a specific antigen), then a population of $10^{12}$ would have to be screened for the expectation of finding one desirable novel gene. Through the use of conventional methods (expressing novel genes via microorganisms), the screening of a large number of new sequences for a specific property is virtually unfeasible, unless the novel gene provides the organism with a distinct growth or survival advantage. Indeed, under the current state of the art, the $10^{12}$ independently transformed microorganisms would have to be screened individually to locate that one desirable novel gene.

Within present screening procedures for detecting novel gene products which are localized within cells, colonies derived from each transformed cell must be treated to break open the cells. Typically 1000–2000 bacterial colonies per standard petri dish are lysed (e.g., by chloroform) for the screening procedure. Thus, to examine $10^{12}$ transformed organisms, 500,000 to 1 billion petri dishes would be necessary. In addition, 10,000 to 100,000 liters of logarithmically dividing cells may be necessary for producing the large numbers of transformable cells.

Alternatively, where a gene product is secreted and attached to the outside of a cell, it may be detected by its ability to bind a fluorescent compound or other marker. In these cases, cell sorters may be used to screen for the synthesis of a novel desirable polypeptide. However, even at a flow rate of 5,000 cells per second, it would take a cell sorter over 60 years to screen $10^{12}$ cells. Thus, present day screening methods which are both extremely costly and time-consuming, effectively prohibit the isolation of novel genes and polypeptide from semi-random sequences.

In addition to the methods briefly discussed above, Fields and Song (*Nature* 340:245–246, 1989) proposed a method for selectably obtaining polypeptides which specifically bind to other polypeptides, using the domains of the yeast GAL4 gene. However, this system has serious limitations. First, only polypeptide-polypeptide binding may be selected; polypeptide-nonpolypeptide interactions are excluded. Second, both the known and novel binding polypeptides have to be expressed in yeast at reasonably high levels and in "native" conformations for the method to have commercial applicability. Third, glycosylated polypeptides or polypeptides that have special modifications may also be excluded by this method. Fourth, it is not clear whether random or semi-random sequences can work, given that they used known polypeptides whose physical interactions were well-established and yet showed only 4.5% of the control GAL4 activity. Fifth, Fields and Song used very large sequences: 633 amino acids of the SNF1 protein and 322 amino acids of the SNF4 protein, which have evolved secondary structures that interact with each other. Sixth, using their method for semi-random sequences of even $10^{10}$ diversity obviates the need for extremely large amounts of DNA, modifying eraJmes, and competent yeast cells.

Contrary to previously disclosed methods, the present invention describes a method for cell-free screening of novel genes and polypeptides. This method avoids the problems associated with large numbers of transformed organisms as well as the limitations of the method disclosed by Fields and Song, and may be completed within a few weeks. Therefore, the methodology allows a substantial time and monetary saving in the isolation of novel gene products.

SUMMARY OF THE INVENTION

Briefly stated, the present invention relates to methods for synthesizing, screening, and selecting high numbers of novel genes and polypeptides. The methods generally comprise the steps of (a) constructing an in vitro expression unit comprising a 5' untranslated region containing an RNA polymerase binding sequence, a ribosome binding sequence, and a translation initiation signal, the expression unit being capable of producing mRNA; (b) attaching one or more semi-random nucleotide sequences to an expression unit; (c) transcribing or replicating the sequences associated with the expression unit and semi-random nucleotide sequences to produce RNA; (d) translating the RNA to produce polysomes under conditions sufficient to maintain the polysomes;

(e) binding the polysomes to a substance of interest; (f) isolating the polysomes that bind to the substance of interest; (g) disrupting the isolated polysomes to release mRNA; (h) recovering and constructing cDNA from the released mRNA; and (i) expressing the gene to produce novel polypeptides.

In one embodiment of the method described above, the process may be repeated on mRNA that has been enriched for desirable sequences by amplifying the RNA or respective cDNA. Subsequently, this amplified subset of genes may be cycled through the various steps outlined above to further enrich for desirable novel genes until desirable sequences represent a significant ($>10^{-3}$) fraction of the truncated population. In principle, the method may be repeated until the population of genes is nearly homogeneous.

Within a second aspect of the present invention, a method for producing novel polypeptides is provided, comprising the steps of (a) constructing an in vitro expression unit comprising a 5' untranslated region containing an RNA polymerase binding sequence, a ribosome binding sequence, and a translation initiation signal, the expression unit being capable of producing mRNA; (b) attaching one or more semi-random nucleotide sequences to the expression unit; (c) transcribing sequences associated with the expression unit and semi-random nucleotide sequences to produce RNA; (d) translating the RNA to produce biologically active polypeptides; (e) subdividing the RNA encoding the biologically active polypeptides; (f) transcribing, translating, and subdividing as set forth in steps (c)–(e) so that the gene of interest is isolated; (g) constructing cDNA from the isolated gene; and (h) expressing the cDNA to produce novel polypeptides.

In yet another aspect of the present invention, a method of producing novel polypeptides is provided comprising the steps of (a) constructing an in vitro expression unit comprising a 5' untranslated region containing an RNA polymerase binding sequence, a ribosome binding sequence, and a translation initiation signal, the expression unit being capable of producing mRNA; (b) attaching one or more semi-random nucleotide sequence to the expression unit; (c) replicating the sequences associated with the expression unit and semi-random sequences to produce RNA; (d) translating the RNA to produce biologically active polypeptides; (e) subdividing the RNA encoding the biologically active polypeptides; (f) translating and subdividing as set forth in steps (d)-(e) such that the gene of interest is isolated; (g) constructing cDNA from the isolated gene, and (h) expressing the cDNA to produce novel polypeptides.

The expression unit described above comprises an RNA polymerase binding sequence, a ribosome binding site, and a translation initiation signal. The expression unit may further comprise a translation enhancer or "activator" sequences, a 3' tail of a selected sequence and appropriate restriction sites. The semi-random DNA sequences may be generated by mechanically, chemically, or enzymatically fragmenting naturally-occurring DNA, by chemically synthesizing the DNA, or by polymerizing the DNA directly onto the expression unit. The substance of interest may be a surface antigen, receptor protein, toxin, organic polymer, active site of a protein molecule, metabolite, antibody, metal, hormone, or other compound.

These and other aspects will become evident upon reference to the following detailed description.

DETAILED DESCRIPTION OF THE INVENTION

The present invention is directed to the isolation of novel genes and polypeptides. These novel genes may have virtually infinite diversity and may code for new polypeptides with commercially important properties, such as novel catalytic activities or the ability to bind selectively to specific substances. Novel genes may be constructed which comprise open reading frames from existing genes or from semi-random nucleotide sequences of chemically synthesized DNA. They may be expressed in a wide variety of organisms using existing promoters, enhancers, initiation codons, plasmids, ribosomal binding sites, and/or terminators. In some cases, it may be advantageous to express the novel genes in vitro, as part of a large-scale production process.

As noted above, the present invention describes a multi-step process for constructing and isolating novel genes and gene fragments which encode novel polypeptides with specific binding and/or biological activities. Within a preferred embodiment, the process comprises the following steps:

1. An expression unit is constructed which contains an RNA polymerase binding sequence (i.e., a promoter or an RNA-directed RNA polymerase initiation site), a ribosome binding site, and a translation initiation signal. The expression unit may also contain convenient restriction sites, translation enhancer or "activator" sequences, and a 3' tail of a selected sequence.

2. Semi-random DNA or RNA sequences are then generated by mechanically, chemically, or enzymatically fragmenting naturally-occurring DNA, RNA, or cDNA sequences, or by chemically synthesizing the nucleotides. The semi-random DNA or RNA sequences are then inserted into the expression unit. Alternatively, the semi-random sequences can be polymerized directly onto the expression unit. A library of $10^{12}$ or greater different sequences may then be created.

3. The novel genes are then transcribed in vitro to produce a pool of RNA copies of the original DNA library. If an RNA-directed RNA polymerase sequence is included, then these replicases may be used to amplify the RNA.

4. The RNA (mRNA) is translated in vitro to produce polysomes. Conditions for maintaining the "polysomes" (RNA-ribosome-nascent polypeptide complexes) are used to keep the desired polypeptide and mRNA together.

5. The polysomes are then allowed to bind to substances of interest, such as surface antigen, receptor proteins, toxins, organic polymers, antibodies, metabolites, hormones, and active sites of protein molecules, or to display biological activity.

6. Polysomes binding to the substance(s) of interest are substantially enriched by the removal of the unbound polysomes. Serial or flow- through washes under conditions which maintain the polysome complexes substantially increase the frequencies of the desired mRNAs, which remain attached to the substances of interest through the polysome structure.

7. The bound/active polysomes are then disrupted to release the mRNAs from the polysome complex.

8. The rare mRNAs are then recovered by making cDNA copies or by direct amplification of the RNA with RNA-directed RNA polymerases. The amplification of the cDNA with DNA polymerase reactions may allow greater ease in recovering these low abundance messages.

9. The resulting cDNAs are then expressed to produce polypeptides.

In most instances, repetition of steps 3–8 is preferable to further increase the frequency of specific binding proteins above a background of nonspecific binding of polysomes.

The isolated, purified novel gene(s) produced by the methods described herein are capable of generating a variety of polypeptide(s) of interest using standard expression techniques, as positive proof that the gene codes for the desired product. In addition, DNA and/or polypeptide sequencing by conventional methods may be used to identify the composition of the novel polypeptide.

Once the polypeptide encoded by the novel gene has been isolated and identified, large-scale production of the novel polypeptide(s) may be accomplished by chemical synthesis (if the amino acid sequence is relatively short) or through recombinant DNA methods, using genetically engineered microorganisms. Alternatively, large-scale in vitro transcription and/or translation methods may be used to produce commercial quantities of the polypeptide.

The DNA sequence coding for the selected polypeptide may also be incorporated into larger genes (i.e., such as into the hypervariable regions of antibody genes) to create hybrid proteins with the specific binding and/or biological activities of the originally isolated novel polypeptides, in addition to other binding and biological activities.

I. THE EXPRESSION UNIT

The expression unit comprises a 5' untranslated region and may additionally comprise a 3' region. The 5' untranslated region of the expression unit contains a promoter or RNA polymerase binding sequence, a ribosome binding sequence, and a translation initiation signal. The 5' untranslated region ("head") may also contain convenient restriction sites and a translation enhancer or "activator" sequence (s). The 3' region may contain convenient restriction sites and a 3' tail of a selected sequence. The expression unit may be chemically synthesized by protocols well known to those skilled in the art. Alternatively, these elements may be incorporated into one or more plasmids, amplified in microorganisms, purified by standard procedures, and cut into appropriate fragments with restriction enzymes before assembly into the expression unit.

The 5' untranslated region contains a promoter or RNA polymerase binding sequence. High-efficiency promoters, such as those for the T7, T3, or SP6 RNA polymerase, are preferred in this invention for the following reasons. Such promoters are short DNA sequences of known composition, are extremely specific for their relative polymerases, and are highly active, allowing for greater than 50 rounds of transcription per DNA template. In addition, T7, T3, and SP6 polymerases are commercially available from many sources and are components of well-characterized transcription kits. For the T7 promoter, the consensus sequence is TAATAC-GACTCACTATAGGGAGA (23 base pairs). Although this sequence is described in conjunction with a preferred embodiment of this invention, it will be evident that related DNA sequences may be used which will function for T7 RNA polymerase, and other sequences will be appropriate for other RNA polymerases. Within certain embodiments, it may be desirable to utilize two promoters, such as both the T7 and SP6 promoters.

Positioned downstream of or within the promoter region is a DNA sequence which codes for a ribosomal binding site. This ribosome binding site may be specific for prokaryotic ribosomal complexes (including ribosomal RNAs) if a prokaryotic translation procedure is used. However, a preferred embodiment of this invention uses a eukaryotic sequence and an in vitro eukaryotic translation system, such as the rabbit reticulocyte system (Krawetz et al., *Can. J. Biochem. Cell. Biol.* 61:274–286, 1983; Merrick, *Meth. Enzymol.* 101:38, 1983). A consensus translation initiation sequence, GCCGCCACCATGG, as well as other functionally related sequences have been established for vertebrate mRNAs (Kozak, *Nucleic Acids Res.* 15:8125–8148, 1987). This sequence or related sequences may be used in the novel gene construction to direct protein synthesis in vitro. The ATG triplet in this initiation seqfience is the translation initiation codon for methionine; in vitro protein synthesis is expected to begin at this point.

Between the promoter and translation initiation site, it may be desirable to place other known sequences, such as translation enhancer or "activator" sequences. For example, Jobling et al. (*Nucleic Acids Res.* 16:4483–4498, 1988) showed that the untranslated "leader sequences" from tobacco mosaic virus "stimulated translation significantly" in SP6-generated mRNAs. They also reported that the 36-nucleotide 5' untranslated region of alfalfa mosaic virus RNA 4 increases the translational efficiency of barley amylase and human interleukin mRNAs (Jobling and Gehrke, *Nature* 325:622–625, 1987). Black beetle virus (Nodavirus) RNA 2 (Friesen and Rueckert, *J. Virol.* 3;7:876–886, 1981), turnip mosaic virus, and brome mosaic virus coat protein mRNAs (Zagorski et al., *Biochimie* 65:127–133, 1983) also translate at high efficiencies. In contrast, certain untranslated leaders severely reduce the expression of the SP6 RNAs (Jobling et al., ibid., 1988).

Appropriate restriction sites may also be included in the expression unit to assist in future genetic engineering. For example, the sextuplet, CCATGG, is the recognition sequence for the restriction endonuclease, NcoI. A NcoI "cutting site" positioned downstream of the ribosomal binding site is a convenient splice point for subsequent genetic engineering. Hence, after purification of a desired novel gene, the expression unit may be spliced from the novel gene at this site, and another promoter may be attached for expression in vivo and large-scale production of the novel polypeptide. The NcoI site may also be used as a convenient cloning site for the construction of hybrid proteins, where two different polypeptide domains are brought together and expressed as a single protein.

In addition, it is most likely advantageous to include in the 5' untranslated region a DNA sequence with at least one restriction endonuclease site for subsequently cloning the novel gene into plasmids. The octameric sequence, GCGGCCGGC, is recognized by NotI nuclease and is particularly useful because it would rarely fall within the novel coding region of the gene (NotI is expected to cut totally random DNA once every 65,536 base pairs). Other restriction sites may also be used; the expected frequency of cutting the novel coding region is dependent upon the nucleotide composition or the DNA source of the coding region. It should be noted that certain palindromic sequences may interfere with translation; however, some sequences may also enhance the rate of translation.

The expression unit may also comprise a 3' region. It is desirable to construct known 3' regions (tails) with palindromic sequences for at least two reasons. First, 3' restriction sites would be convenient for any later genetic engineering of the polypeptide coding region. For example, if NotI sites were located in both the 5' and 3' regions, a desirable polypeptide coding sequence could be cut out with NotI "sticky ends" for further cloning. Second, palindromes may cause secondary structures which impede translocation, thus, palindromes in the 3' region may slow down the movement of ribosomes during translation. This second property may be desirable for preventing ribosomes from "falling off" the mRNA and thereby enhancing the number of polysomes in the in vitro translation step. The 3' region may also contain a poly-A or other polynucleotide stretch for later purification of the mRNA from other components in the in vitro translation reaction by hybridization to a complementary homopolymeric sequence.

In addition, other nonrandom sequences may be incorporated into the expression unit. Within one embodiment, the expressed polypeptides contain both nonrandom and semirandom amino acid sequences. The nonrandom component of the coding region is synthesized and produced with the nonrandom 5' untranslated region and/or with the 3' region. This nonrandom coding sequence specifies a string of amino acids (an identification or "ID" peptide) that is conserved among the billions of novel polypeptides. The ID peptide would be useful for quantifying the amount of novel polypeptide and for purification of the novel polypeptide (given that an antibody against the ID peptide is available or can be produced). One example is the 11 amino acid Substance P, which can be attached as a fusion peptide to other polypeptides. Anti-Substance P antibodies are commercially available for detecting and quantifying fusion proteins containing Substance P. Another example is the eight amino acid marker peptide, "Flag" (Hopp et al., *Bio/Technology* 6:1204–1210, 1988).

Amino-terminal ID peptides have at least two advantages over carboxy-terminal ID peptides. First, it is easier to make gene constructions which maintain the proper reading frame of the N-terminal ID, because long stretches of semi-random DNA or RNA will tend to end in all three reading frames for a C-terminal ID. Second, the N-terminal ID may be designed to function as a signal peptide in a transformed organism, allowing for the possible secretion of the novel polypeptide during large-scale production.

Nevertheless, C-terminal ID polypeptides may also be used. One preferable C-terminal polypeptide is polyglycine, which is encoded by poly-dG and is read Gly-Gly-Gly, etc., regardless of the reading frame of the semi-random sequences. The polyglycine 3' end of the polypeptide may act as a noninterfering tether of the nascent peptide and allow the semi-random sequences greater access to bind molecules of interest. In addition, the poly-dG sequence may be used for priming second strand synthesis of the cDNA and may be useful for purification of the RNA or DNA with polyC or poly-dC. Other repetitive sequences, such as GGGCGGGC . . . , may be used to code for a recognizable peptide sequence which is expressed in all reading frames. A preferable form of the ID peptide is one which may be cleaved from the novel polypeptide by simple chemical or enzymatic means.

In addition to the DNA expression unit, an RNA expression unit may be constructed for semi-random polypeptide synthesis. One possible advantage of the RNA expression unit is that the recovery of the polysomal mRNA does not have to go through an initial cDNA stage. Instead, the mRNA with the desired sequences may be amplified with an RNA-directed RNA polymerase, such as that of QB (Q Beta) replicase (Haruna and Spiegelman, *Proc. Nat. Acad. Sci.* 54:579–587, 1965). This enzyme can make one billion copies of recombinant RNA in 30 minutes (Lizardi et al., *Bio/Technology* 6:1197–1202, 1988). One suitable cloning strategy for amplification of recombinant RNA is detailed in Lizardi et al. (ibid., 1988). For purposes of the present invention, other elements, such as restriction sites, enhancers, and ID sequences, may be added to the DNA plasmids which give rise to the QB RNA templates. Semi-random coding sequences may be inserted on these plasmids by standard DNA methodologies. When the QB replicase template is transcribed (for example, by T7 RNA polymerase), an RNA library capable of in vitro replication may be created which contains the semi-random gene sequences. Alternatively, a similar RNA expression unit may be constructed by chemically synthesizing the appropriate RNA molecules and assembling them via an RNA ligase, such as the T4 RNA ligase (commercially available), which links together single-strand RNA and/or single-strand DNA.

II. SEMI-RANDOM NUCLEOTIDE SEQUENCES

Semi-random sequences of DNA or RNA are attached to the expression unit. Since the RNA expression units and semi-random sequences may be generated from a DNA template or constructed from chemically synthesized RNA or mRNA fragments in much the same manner as DNA expression units, the following description merely describes the process for semi-random DNA attachment to the expression unit. Those skilled in the art will readily be able to construct the RNA-equivalent of the expression units attached to semi-random polynucleotides.

Semi-random DNA may be generated by at least three methods. First, naturally-occurring DNAs from virtually any living source may be mechanically, chemically, or enzymatically fragmented and attached to the 5' untranslated region with DNA ligase. Mixtures of fragments from different DNA sources may be used. The end result may be the selectable expression of an active "open reading frame"—a portion (fragment) of a protein that has no "nonsense" (or "stop") codon, unless the activity resides in the extreme C-terminus of the molecule. In one embodiment of this invention, a gene coding for a known function may be fragmented; the resulting pieces are ligated to the 5' untranslated region and later screened for the expression of activity in the polysome assay. By examining the smallest gene fragment which provides biological activity, an analysis of protein domains may be made. Gene fragment analysis may be useful for creating small biologically active peptides and hybrid therapeutic proteins and may be beneficial for drug delivery, if smaller size assists the peptide in reaching the target site.

In another embodiment of the present invention, the "fragmented" DNAs may be semi-randomly sized cDNA molecules from a cDNA library. By expressing cDNAs in vitro and using polysome selection, a very rare partial or perhaps even full-sized gene may be isolated through binding the polysome to antibody, receptor protein, or other diagnostic molecule. The cell-free expression of cDNA "fragments" as herein described may be orders of magnitude more sensitive than previously described methods in locating desirable cDNA clones.

A second method for generating semi-random DNA is to chemically synthesize the DNA. For example, relatively long DNA molecules of approximately 100 nucleotides may be synthesized with mixtures of nucleotides at each position. However, a statisical problem of nonsense codons becomes apparent with chemically synthesized DNA. For the gene fragments and cDNA strategies described above, an active, open reading frame is located from within existing protein sequences. "Open reading frame" implies that no stop codon exists and often indicates a sequence from within a protein coding region.

However, it should be noted that chemically synthesized DNA having enough diversity to code for all 20 common amino acids at all positions may not necessarily have open reading frames. The stop codons—TAA, TAG, and TGA—represent three of the 64 possible DNA triplets. For completely random DNA, with the equal likelihood of any of the four nucleotides in each position, the probability of a nonsense codon is therefore $3/64=4.6875\%$. For a random DNA stretch coding for a string of 30 amino acids, the probability of at least one stop codon within that string is about 76%. Stop codons cause termination of translation and release of the nascent polypeptide from the ribosome complex. Therefore, strategies to reduce the frequencies of nonsense codons and to bypass the usual result of nonsense codons during protein translation are preferable, and discussed below.

More specifically, the A, T, C, and G base composition may be manipulated to favor certain codons and in particular to reduce the likelihood of nonsense codons. In the extreme case, the third position of each triplet codon may be synthesized with only C and T to theoretically avoid nonsense codons. However, in this case not all 20 amino acids are encoded. Lim and Sauer (*Nature* 339:31–36, 1989) have used an equal mixture of all four bases in the first two codon positions and an equal mixture of C and G at the third codon position in synthesizing new regions of lambda repressor. This combination allows for any of all 20 amino acids at each codon and reduces the frequency of nonsense triplets to $1/32=3.125\%$. However, in a string of 30 amino acids the likelihood of at least one TAG stop codon is about 61%.

In a preferred embodiment of this invention, unequal mixtures of the bases are used in all three codon positions to reduce the frequency of stop codons, while still allowing a high frequency of all 20 amino acids at all codons. In the first codon position equal molar amounts of C, A, and G are used, but only half that amount of T is used. In the second codon position the amount of A is reduced to half of the level of the other three bases. In the third codon position only G and C are used, and in equal molar amounts. The result of this strategy is a greater than 79% probability that no stop codons will be present in a string of 30 amino acids. The proportions of the individual amino acids are slightly distorted in this case relative to a totally random DNA strategy. However, only tyrosine will be represented at less than half of the expected frequencies compared to the random situation.

To further overcome the presence of nonsense codons when using chemically synthesized DNA, it is preferred that nonsense suppressing tRNAs be used in the in vitro translation steps. In particular, since the strategy described above eliminates all but the TAG stop triplet, and tyrosine codons are underrepresented as the result of unequal mixtures of bases at each codon position, a nonsense suppressor which recognizes TAG (actually UAG in the mRNA) and inserts tyrosine into the growing polypeptide chain is most desirable. Such tyrosine-inserting nonsense suppressors may be generated by changing the anticodon region of a tyrosyl-tRNA in such a manner that the tyrosyl-tRNA now "reads" UAG instead of the normal UAU and UAC tyrosine codons in mRNA. Normal tyrosyl-tRNAs will also be included in the translation step to read the tyrosine codons. Nonsense suppressors can also be made for the other two nonsense codons. As an example, tryptophane- or leucine-inserting suppressors of the UGA stop codon have been well characterized—as have many other nonsense suppressors. The nucleotide sequences of many nonsense suppressors are known; and, therefore, the construction of such molecules would be evident to those skilled in the art.

Nonsense suppressors of mammalian translation systems are known (Burke and Mogg, *Nucleic Acids Res.* 13:1317–1326, 1985; Capone et al., *EMBO J.* 4:213–221, 1985; Diamond et al., *Cell* 25:497–506, 1981; Hudziak et al., *Cell* 31:137–146, 1982; Laski et al., *EMBO J.* 3:2445–2452, 1984). Additionally, different investigators have shown that the "reading" of nonsense codons in eukaryotic in vitro translation systems is possible with the use of suppressor tRNAs, including the tyrosine-inserting UAG suppressor tRNA from yeast (Capecchi et al., *Cell* 6:269–277, 1975; Gesteland et al., *Cell* 7:381–390, 1976). Readthrough of the UAG stop codon by such yeast suppressors has been reported as high as 70% in vitro (Pelham, *Nature* 272:469–471, 1978). Geller and Rich (*Nature* 283:41–46, 1980) have successfully suppressed nonsense codons in reticulocyte systems with yeast suppressor tRNAs and with bacterial suppressor tRNAs and tRNA synthetase. Therefore, the use of tRNA suppressors in the present invention to reduce premature release of polypeptides from the ribosomes during the translation step is well within the state of the art. Furthermore, both Pelham (ibid., 1978) and Geller and Rich (ibid., 1980) describe high levels of naturally-occurring nonsense suppression in eukaryotic translation systems. In particular, Pelham shows that a particular UAG codon in tobacco mosaic virus may be "read" (suppressed) nearly 40% of the time by "supraoptimal concentrations of $Mg^{+2}$," or a reported 2.1 mM $MgCl_2$. This level of magnesium ion or higher may therefore be used advantageously within the present invention to increase the readthrough of nonsense codons and to thereby reduce the problem of translation termination of longer semi-random nucleotide sequences.

Second-strand synthesis of these artificial nucleotide sequences may be accomplished by "random priming" and extension with DNA polymerase and/or by including a poly-dX tail from which to prime with poly-dX'. Other methods, such as the use of terminal palindromes that create "hairpin loops" for self-priming, may be used for second strand synthesis. 100 μg of double-stranded DNA of 100 nucleotides contains about $10^{15}$ molecules. If the semi-random synthesis strategy is used, the expectation is that each of these molecules codes for a different polypeptide. Therefore, a very large diversity in coding potential exists within laboratory bench-scale amounts of DNA. Such a synthetic DNA molecule of 100 nucleotides is merely provided for purposes of illustration; longer sequences may also be synthesized. In addition, shorter synthetic molecules may be generated and ligated together to make semi-random sequences of any given length. Shorter molecules are expected to preserve the reading frame of the synthetic DNA better than longer molecules, because each addition of chemically synthesized base is not 100%. Therefore, more nonsense codons may be avoided by the use of shorter artificial DNA molecules. T4 RNA ligase or other means may be used to link together the short single-stranded DNAs.

A third method for generating semi-random DNA is to polymerize the molecules directly onto the 3' end of the 5' untranslated region. If no N-terminal ID sequence is used, the polymerization may occur immediately after the ATG initiation sequence or preferentially after the ATGG sequence—which preserves both the consensus vertebrate initiation site and the NcOI site. The most commonly used enzyme for this polymerization is terminal transferase (usually from calf thymus), which is routinely used for generating homopolymeric regions for DNA cloning. However, by mixing different deoxynucleotide triphosphates, semi-random heteropolymers of DNA may be synthesized on a DNA primer with a free 3'-OH. Again, the A, T, C, and G base composition may be manipulated to favor certain codons and reduce the frequencies of nonsense codon by controlling the relative concentrations of the four deoxynucleotide triphosphates. In particular, a lower amount of dATP should reduce the frequencies of nonsense codons (TAA, TAG, and TGA). *E. coli* DNA polymerase I is reported to carry out non-template (de novo) synthesis of DNA and may be used instead of terminal transferase (A. Kornberg, *DNA Replication*, W. H. Freeman & Co., San Francisco, Calif., 1980). Other enzymes or chemical methods may also polymerize DNA directly onto the expression units. Second-strand synthesis is most easily accomplished by random primer extension, but other methods may provide the same result. Again, the use of nonsense suppressing tRNAs may greatly assist in overcoming the problem of stop codons in this semi-random DNA sequence.

III. TRANSCRIPTION OF THE NOVEL GENES

If DNA expression units are used with the semi-random sequences, mRNA may be easily created with RNA polymerase. As discussed above, T7, T3, and SP6 RNA polymerases are commercially available and extremely active. As an example, a DNA expression unit with a T7 promoter is treated with T7 RNA polymerase according to manufacturers' specifications. Approximately 50 mRNA copies may be synthesized routinely for each DNA molecule in 30 minutes. The DNA may be degraded with RNase-free DNase. If the original DNA library had a sequence diversity of $10^{12}$ molecules, the resulting mRNA pool should reflect the same level of diversity but now contain 50 or more RNA copies of each different DNA molecule. An RNA library of 6 μg may contain 50 copies of $10^{12}$ different mRNAs that are each capable of expressing a semi-random polypeptide of 30 amino acids. Since 6 μg is easily manageable in small test tubes, standard laboratory tools and vessels may be used.

The 5' ends of mRNAs need to be modified with the addition of diguanosine triphosphate "caps" (or analogs) for efficient translation in eukaryotic systems. The 5' capped mRNA may be generated during in vitro transcription (Hope and Struhl, *Cell* 43:177–188, 1985) and/or in the in vitro translation process (Krieg and Melton, *Nucleic Acids Res.* 12:7057–7070, 1984). To cap messages during transcription, an excess of diguanosine triphosphate or an analog thereof (m7G(5')ppp(5')G, from Boehringer Mannheim Biochemicals, for example) is used during the RNA polymerization relative to GTP. An mRNA capping kit based on this method is commercially available from Stratagene (California), which claims that 90%–95% of the resulting RNA is capped.

If the expression unit is RNA-based, such as the QB replicase system, a few RNA copies may be generated with T7 or other promoter systems (see Lizardi et al., ibid, 1988) if the novel gene constructions involve a DNA plasmid. Once RNA copies exist (or if the novel genes were assembled at the RNA level), RNA-directed RNA polymerase is capable of making a virtually unlimited number of copies of the RNA library (one billion copies are easily attainable). However, the diversity of the library remains the same. With RNA phages, such as QB, the library may be self-sustaining at the RNA level without the necessity of going through a DNA intermediate.

IV. TRANSLATION OF THE RNA

Several in vitro translation methods are widely known. For convenience, the rabbit reticulocyte methods may be used with minor modifications. In vitro translation kits are available commercially. For example, the "Translation Kit, Reticulocyte, Type I" from Boehringer Mannheim Biochemicals has all components for 100 translation reactions. Each reaction has been optimized for approximately 1 µg of mRNA in a 25 µl volume. One µg of mRNA is sufficient to code for over $4 \times 10^{12}$ novel genes, as described above. Therefore, it is possible to translate extremely high numbers of novel genes in relatively small volumes. For example, $10^{13}$ 80S ribosomes only weigh approximately 66 µg. Because of the small size of the mRNA, only a few ribosomes per message are expected to saturated the mRNAs.

As described in the protocol for the representative translation kit noted above, GTP and m7G(5')ppp(5')G are required for the efficient translation of in vitro transcribed RNA. Even if mRNA capping has been previously performed during transcription, as described above, it may be advantageous to add the diguanosine triphosphate (or analog thereof) and guanylyltransferase (Krieg and Melton, ibid., 1984) to the translation reaction. In the absence of capping during transcription, the two reagents are necessary for the efficient translation of the mRNA. In particular, when QB constructions are translated, diguanosine triphosphate (or analog thereof) and guanylyltransferase may be necessary for capping the RNA molecules during translation.

Other techniques may also be employed to optimize translation and especially ribosome attachment to the mRNAs. For instance, it may be desirable to add ribonuclease inhibitors, such as heparin. Eukaryotic systems, such as the wheat germ and reticulocyte translation methods, may yield similar results to prokaryotic systems. The prokaryotic systems have the advantages of smaller ribosomes and more readily available nonsense suppressor tRNAs. In addition, in prokaryotic cells transcription and translation are often simultaneous reactions. In the absence of coupled transcription and translation in prokaryotes, mRNA stability is greatly reduced. Therefore, a prokaryotic in vitro expression system may be used which combines transcription and translation.

As described above, a preferred embodiment of the present invention is the use of suppressor tRNAs (especially tyrosine-inserting suppressors), which may be produced through recombinant DNA technology and/or by the partial purification of these molecules from mutant cell lines. Radioactive amino acids, especially S35-methionine, may be useful for monitoring in vitro translation and for following low amounts of polysomes in subsequent steps.

After about 30–60 minutes, protein synthesis begins in the translation reactions. The precise time may be determined for any given set of translation conditions by the use of radioactive amino acids (such as S35-methionine) and monitoring TCA precipitable counts, which is indicative of polypeptide synthesis. After the onset of protein synthesis, cycloheximide at a final concentration of 1 µg/ml is added to prevent the movement of the ribosomes on the mRNAs (Lynch, *Meth. Enzym.* 152:248–253, 1987). This level of cycloheximide and a $Mg^{+2}$ concentration of 5 mM may be use to maintain the mRNA-80S ribosome-nascent polypeptide complexes (polysomes). Other ribosome inhibitors may also be used since cycloheximide, for example, will not work on prokaryotic ribosomes. However, in the absence of GTP the polypeptide release from the ribosomes should not normally occur.

V. BINDING POLYSOMES TO SUBSTANCES OF INTEREST

The list of potential compounds to which the nascent peptide might bind is virtually unlimited. The coupling chemistries to link these compounds to columns, matrices, filters, beads, etc., will depend to a great degree upon the nature of the compound. In some cases, whole cells or cellular fractions may be used to find peptides which bind to cellular components, such as receptor proteins and other membrane-bound molecules.

For many proteins and nucleic acids, binding to nitrocellulose or similar artificial surfaces is a property of the filters or fibres. In these cases, the substances of interest are "stuck" to the membranes by established protocols. Bovine serum albumin (BSA), gelatin, casein or nonfat milk, or other proteinaceous material is then typically added in excess to bind up any "free" surface sites. For example, an antibody is first bound to nitrocellulose by placing a solution of the antibody on a nitrocellulose disk in a microtiter dish. After absorbing the antibody to the nitrocellulose, the disk is washed by moving the nitrocellulose disk to fresh microtiter dishes containing saline. After the washes, the disk is placed in a microtiter dish containing gelatin in solution. The disk is then washed again with saline.

Before allowing the polysomes to bind substances of interest, it may be desirable to pre-absorb the polysome mix against BSA, gelatin, and in particular the proteinaceous material (blocking protein) used in excess as described above. In this manner, polysomes which bind to the blocking protein or nonspecifically to any protein are removed. This pre-absorption step will lead to much greater specificity of polysomes binding to the substance of interest. For binding to specific antibodies (as in the case above), the pre-absorption step(s) may include another antibody, preferably of a similar subclass, but having different variable/hypervariable regions. By screening out polysomes which bind generally to antibodies but not to the variable/hypervariable region, the present invention may be useful for selecting anti-idiotypic binding proteins. Such molecules may have biological or enzymatic activity (as seen for some anti-idiotypic antibodies) or be useful as vaccines.

The binding of polysomes to substances of interest may be accomplished in the presence of $MgCl_2$ (5 mM) and RNase inhibitors, such as heparin. In addition, specific incubation parameters—such as low or high temperature, high or low salt, or different pHs—may be used to locate polypeptides which bind conditionally, depending on the environment. Incubation times will depend upon the concentration of the bound substance of interest and upon the nature of such substance.

VI. ISOLATION OF POLYSOMES WHICH BIND TO SUBSTANCE(S) OF INTEREST

After allowing the polysomes to selectively bind to the substance(s) of interest, nonbinding polysomes are generally removed by washings. This wash should contain $MgCl_2$ and perhaps gelatin, BSA, or other proteins to help reduce nonspecific binding of polysomes. If radiolabeled amino acids are used in the translations, washes (serial or flow-through) should continue until little detectable change is observed in radioactive counts bound to the substance of interest. If the amino acids are not labelled, washes should continue until at least $10^{-6}$ dilution of the polysome solution is obtained.

Conditionally-binding novel peptides may be isolated after these washes by shifting the polysomes into the desired environment for nonbinding, such as higher temperature, different pH, high metal ion concentration, or low salt concentration. Those peptides (and their attached ribosome mRNA complexes) which do not bind under the second ("stringent") condition(s) will be released into the solution and represent potential conditionally-binding factors against the substance of interest. Once immobilized, conditionally-binding peptides may be used to purify substances of interest. Alternatively, conditionally-binding peptides may serve as reagents in monitoring environmental changes.

VII. DISRUPTION OF THE ISOLATED POLYSOMES

The isolated (bound) polysomes may be easily disrupted by the removal of $Mg^{+2}$ (by dilution or via chelating agents) or through the destruction of proteins by a number of methods (proteases, chloroform, etc.). Although dilution is the easiest method, it may not result in as thorough a disruption of the polysomes as compared to other methods. The bound polysomes are placed in a solution lacking $Mg^{+2}$ to liberate the mRNA; RNase inhibitors may be desirable.

Conditionally-binding polysomes, which were released under any of the desired environments, may be treated in a similar fashion to disrupt the polysomes and release their mRNAs.

VIII. RECOVERING MESSENGER RNA AND CONSTRUCTING cDNA

Theoretically, if a single polysome binding to the substance of interest carries a mRNA, its rare mRNA is capable of being isolated (recovered) from the entire library of mRNAs. The mRNA may also be amplified by several techniques in order to facilitate isolation.

The use of the polymerase chain reaction (PCR) on a single copy of DNA and on rare mRNA is well documented. (For review, see H. A. Erlich (ed.), PCR Technology, Stockton Press, New York, N.Y., 1989; M. A. Innis et al. (eds.), PCR Protocols: A Guide to Methods and Applications, Academic Press, San Diego, Calif., 1989; H. A. Erlich (ed.), Polymerase Chain Reaction: Current Communications in Molecular Biology, Cold Spring Harbor Press, Cold Spring Harbor, N.Y., 1989.) Briefly, the rare mRNA is first subjected to cDNA synthesis by standard means. Since the sequences of the 5' and 3' regions are known, specific primers may be used for cDNA synthesis. Second, the single cDNA may then be amplified through the use of specified primers (even the same primers as those used in cDNA synthesis). The primers used for PCR may include sequences which restore the 5' and 3' regions of the original expression unit—that is, sequences which restore the promoter (e.g., the T7 polymerase recognition sequence) and 3' region are desirable. By recreating the expression unit in this manner, repeated rounds of transcription-translation-polysome selection may be performed until virtually all of the selected genes code for binding peptides. For expression units based on RNA phages, such as QB, recovery and amplification of the rare mRNA is simplified because each mRNA may be capable of replication to one billion copies or more, using the appropriate replicases.

IX. EXPRESSION OF NOVEL GENES

Once the novel genes have been isolated and sequenced, they or related sequences may be (1) cloned, (2) chemically reproduced, (3) mutated, and (4) expressed by protocols well known in the art. Large-scale production of the novel polypeptide may be accomplished through recombinant DNA methods, using genetically engineered microorganisms. A large variety of prokaryotic and eukaryotic expression systems exist for the in vivo synthesis of the novel binding peptide. The convenient NcoI site described above or other restriction sites may be used to connect the coding region of the novel gene to a desired promoter. It will be evident to those skilled in the art that other gene splicing strategies exist as well. A translation stop codon and a transcription termination sequence may be added to the 3' end of the novel gene for proper expression of the gene in a microorganism. This genetically engineered sequence may then be placed on a plasmid or vector and placed within a desired host cell by transformation, transduction, infection, electroporation, microinjection, or other similar methods. The novel peptide sequence may be attached to a signal sequence for possible secretion from the microorganism and/or may contain ID peptides, as herein described, for quantifying and purifying the resulting gene product. The novel peptide or related sequence may be attached to other translated sequences to form a hybrid or fusion protein which is similarly expressed in a genetically engineered organism. Alternatively, large-scale in vitro transcription and translation methods may be used to produce commercial quantities of the polypeptide.

Finally, if the amino acid sequence of the novel peptide is relatively short, currently available technologies allow for the large-scale chemical synthesis of the polypeptide. Chemical synthesis of the novel peptide has advantages over the in vitro and in vivo expression systems. Among these advantages chemical synthesis (1)is a better defined and therefore more reproducible system for synthesis, (2) has no contaminating sources of DNA and RNA, (3) has no contaminating sources of nucleases, proteases, and other modifying enzymes, and (4) provides a relatively pure product after synthesis.

X. REPETITIVE ENRICHMENT FOR SPECIFIC POLYSOMES

Depending upon the amount of background, nonspecific binding of polysomes to the substance(s) of interest, one may choose to perform a few to many cycles of translation-transcription-binding-recovery as described above to increase the frequency of sequences which code for the desired polypeptide. For example, if each cycle increases the frequency of the desired novel gene(s) by $10^4$, then three cycles may be sufficient for isolating a sequence which exists in the original library at a frequency of $10^{-12}$. Each cycle may be completed in one day; and many steps of the process may be performed by automated workstations, or robots. Therefore, many cycles may be routinely accomplished for a desired binding activity within one week.

XI. SCREENING FOR ACTIVITIES OF TRANSLATED PRODUCTS WITHOUT POLYSOME BINDING

One aspect of the present invention does not require polysome binding for gene isolation. Instead, in vitro translation is allowed to proceed to completion, with the resultant release of the new polypeptides from the ribosome. This is accomplished by the use of nonsense codons or by the ribosomes "falling off" the end of the mRNAs. The new peptides may be separated from the ribosomes and other components of the translation reaction by gel filtration and/or centrifugation and/or other means, in order to concentrate the translation products. The peptide mixture is then challenged to exhibit biological or enzymatic activity—for example, the peptides are assayed for mitogenic activity by treating tissue culture cells lacking a growth factor.

If biological or enzymatic activity is observed within the entire array or subset of the novel peptides, the gene(s) which codes for this activity may be located by subdividing the original library or an RNA copy of the library and screening for activity in a subdivision. After successive subdivisions, the desired gene may be isolated to a pool containing (for example) less than 1,000 different sequences. In theory, the desired gene may be completely isolated by subdivision (to a "pool" containing just that one gene). With PCR, QB replicase or other methods (as described above), the desired sequences may be amplified to a level where in vitro transcription and translation produces a highly enriched peptide solution having the biological/enzymatic activity. At a frequency of 1 to $10^{-3}$, the gene of interest may be readily isolated and cloned into appropriate expression systems, using methods currently available.

XII. CELL-FREE IDENTIFICATION OF NOVEL GENES AND PEPTIDES

After a novel gene with putative binding or biological activity has been isolated, it may be demonstrated that the purified sequence codes for the activity of interest by amplifying the DNA and/or RNA so that sufficient mRNA is produced for larger-scale in vitro translation. The translation products of this purified sequence should be nearly homogeneous polypeptides having the assayable activity. The gene and/or the polypeptide may be sequenced by existing methods to establish the composition of the novel polypeptide. Alternatively, the purified gene may be cloned into microorganisms for amplification and expression. Subsequently, biological/binding activities as well as sequence identity may be established for the novel gene and polypeptide.

XIII. CREATING NOVEL HYBRID PROTEINS

After the nucleic acid sequence has been determined for the novel gene, this sequence may be incorporated into larger genes to create hybrid proteins, which have the characteristics of the novel peptide and other desirable properties. One class of hybrid proteins which may be created by this technology is characterized by specific binding to cells and cytotoxic abilities. For example, a cell surface receptor-binding peptide may be joined to ricin or other toxins via DNA splicing methods. This type of hybrid protein may be used to selectively kill different cell types, including pathogens and tumor cells. The gene which encodes the hybrid protein may be completely synthesized or result from splicing the appropriate gene fragments together. This gene may be expressed in a variety of expression systems.

A preferred embodiment of this invention is the replacement of variable and hypervariable regions of antibody and antibody-like genes by novel gene sequences which code for binding activities against substances of interest. In this manner, a much greater range of diversity is possible against antigens of interest; and the screening process may be much more efficient and time-saving than the production methods for monoclonal antibodies against the same antigens. These "custom" hybrid antibody genes may be expressed in a number of organisms to produce active antibodies with new specificities or properties.

XIV. OTHER COMMERCIAL USES OF THE INVENTION

The application of the present invention in diagnostic tests parallels the use of monoclonal/polyclonal antibodies, and is more advantageous, primarily because the isolation of novel polypeptides as herein described may take considerably less time (one week versus a few months for antibodies). In addition, other advantages may be seen. The novel polypeptides may be considerably smaller molecules than the antibodies. Therefore, synthesis, purification, and/or manufacturing of the novel peptides may be greatly simplified and cost-effective as compared to antibodies. The smaller size may also aid in stability, formulation, and in reaching the target molecules.

The novel polypeptides may be identifiable by (1) fusing them to a biologically active peptide which has a quantifiable activity (such as peroxidase or other enzymatic activity), (2) synthesizing them with an ID peptide, described above, to which existing antibodies are known to bind, (3) radioactively labelling them, (4) chemically adding markers, such as fluorescent dyes or metallic substances, or (5) any combination of the above. To increase specificity in the diagnostic use of the novel polypeptides, two or more different polypeptides may be used. In addition, novel polypeptides may be used as competitive binding elements in diagnostic tests which rely upon competitive binding to antigens or substrates.

Another advantage of novel polypeptides generated via the present invention is that they may bind to many classes of molecules which would not elicit a strong immune response, because some molecules are not complex enough or are too similar to an organism's resident compounds to trigger antibody formation. In addition, the use of novel polypeptides in diagnostic binding assays may have a much greater scope than the traditional antibody-based methods.

The novel polypeptides of the present invention may also be used therapeutically as originally isolated or as part of fusion proteins. For example, if a novel polypeptide were selected to bind a given toxin, it might also neutralize the toxin. If a new polypeptide is bound to a viral receptor site on a cell membrane or to the virus's attachment mechanism, infection of the cell may be diminished. As described earlier, fusion proteins carrying novel polypeptide recognition sequences in addition to a toxin may be used to selectively kill diseased or malignant cells. The binding of novel sequences to infected or malignant cells may trigger an immune response against the cell-peptide complex and, therefore, may be useful in the control of disease.

EXAMPLES

The following examples are provided by way of illustration and not by way of limitation. Within the examples, standard reagents and buffers that are free from contaminating activities (whenever practical) are used. It is preferred to exercise care to avoid ribonucleases and PCR product contamination.

EXAMPLE 1

SYNTHESIS OF A NOVEL GENE LIBRARY

The sequences and strategies for creating a novel gene library require careful planning by those skilled in the art. The 5' untranslated region of the expression unit contains an RNA polymerase site, a ribosome binding site, an initiation codon, and selected 5' untranslated sequences. The polymerase binding site used in this example is the T7 promoter sequence: TAATACGACTCACTATAGGGAGA (23-mer), which is placed at the 5' end of the expression unit.

A rabbit reticulocyte system is used for translation of the RNAs synthesized from the T7 promoter. Therefore, the ribosome binding site should include at least part of the consensus sequence for eukaryotic untranslated regions. In her review article, Kozak (ibid., 1987) suggests that very short untranslated regions (less than 10 nucleotides) do not initiate protein synthesis efficiently. A selected untranslated region of 36 nucleotides is used here. This untranslated region is derived from the naturally-occurring (36-base pair) upstream sequence of the adult rabbit hemoglobin (alpha-globin):

ACACTTCTGGTCCAGTCCGACTGAGAAGGAACCACC
ATGG, where the underlined ATG represents the start of translation at a methionine initiation codon (Baralle, *Nature* 267:279–281, 1977). The rabbit alpha-globin untranslated sequence is chosen because (1) it is expected to be a favorable substrate in a rabbit reticulocyte system and (2) it contains the important "motifs" of Kozak's model mRNA.

The alpha-globin sequence is modified in the following ways for in vitro gene expression. First, the 5' A (underlined above) is replaced by a G, which may aid in the capping of the mRNAs (Green et al., *Cell* 32:681–694, 1983). Second, the G (underlined in the alpha-globin sequence) is replaced with an A to help eliminate a putative secondary structure in the untranslated region of alpha-globin which is hypothesized to reduce the initiation of protein synthesis by 60% relative to the beta-globin mRNA (Baralle, ibid., 1977). This second change also creates a convenient GATC restriction site in the 5' untranslated region. The resulting leader sequence, including the ATGG of the coding region, is therefore the following:

GCACTTCTGATCCAGTCCGACTGAGAAGGAACCACC
ATGG.

This leader sequence is placed immediately downstream from the T7 promoter.

The 3' region contains (1) a selected sequence for specific-primer-directed DNA synthesis, (2) a GGG-rich region which codes for a polyglycine tether that gives the nascent polypeptide spatial freedom to bind the substance of interest, and (3) convenient restriction sites whose resulting RNA secondary structure may impede the translocation of ribosomes off the mRNA. The polyglycine region comprises 20 codons for glycine; most of the glycine codons are adjacent GGG triplets, which code for glycines in all reading frames. However, some of the glycine codons are GGT or GGA to keep the DNA strands in proper register. The restriction sites for Bam HI (GGATCC) and NotI (GCGGCCGC) are chosen to be placed very near the 3' end of the gene; in the mRNA these sequences are expected to form hairpin loops. To prevent second-strand self-priming (of hairpin loops) by the NotI sequence, an addition of AAAA is made at the 3' end. The 3' region therefore has a general sequence of (GGG or GGT/A)$_{20}$ followed by GGATCCGCGGCCGCAAAA. A specific sequence for this region is given below.

The semi-random gene sequence is synthesized with known 5' and 3' ends which undergo basepairing and ligation with the fully described 5' untranslated region and 3' region segments. To achieve this end, the semi-random gene is synthesized with a 5' CACCATGG, which may basepair with the octamer CCATGGTG on the complementary strand of the 5' untranslated region. The initiation (first) codon, ATG, is necessary for translation of the semi-random sequences. The subsequent G is the first position of the second codon and is constant to preserve the NcoI site at the front end of the gene. The rest of this second codon and the next 28 codons are synthesized following the rules outlined earlier for reducing nonsense triplets. That is, in the first codon position, equal molar amounts of C, A, and G are used but only half that amount of T is used. In the second codon position, the amount of A is reduced to half of the level of the other three bases. In the third codon position, only G and C are used, and in equal molar amounts.

After codon 30 is synthesized, GGTGGGGG is added. This sequence codes for two glycine residues and is used to ligate the semi-random sequences to the 3' region, which has a complementary CCCCCACC overhang on the opposite strand. The result of this synthesis is a sequence that codes for virtually all 30 amino acid polypeptides (beginning with methionine) and has a polyglycine tether. The probability of no stop codons in this string of triplets is approximately 80%. By using partially purified yeast tyrosine-inserting UAG suppressor tRNA (Pelham, ibid., 1978) during the subsequent translation, over 90% of the semi-random sequences are expected to code for full-length polypeptide.

The specific oligonucleotides to synthesize are listed below:

---

1. T7 Promoter & "Globin" Leader (for gene synthesis and PCR):
   5'TAATACGACTCACTATAGGGAGAGCACTTCTGATCCAG
   TCCGACTGAGAAGGAAC3'-OH
II. Anti-T7 Promoter & "Globin" Leader (for gene synthesis):
   5'CCATGGTGGTTCCTTCTCAGTCGGACTGGATCAGAAGC
   TCTCCCTATAGTGAGTCGTATTA3'-OH (5' kinased with T4 Polynucleotide Kinase)
III. Semi-Random Gene (for gene synthesis):
   5'CACCATGG . . . semi-random as described . . . GGTGGGGG3'-OH (5' kinased with T4 Polynucleotide Kinase)
IV. Poly-Glycine & 3' Restriction Sites (for gene synthesis):
   5'TGGGGGTGGTGGGGGGGGGGGGGGAGGAGGGGGGG
   GGGGAGGGGGAGGTGGTGGATCCGCGGCCGCAAAA3'-OH (5' kinased with T4 Polynucleotide Kinase)
V. Anti-Poly-Glycine & 3' Sites (for gene synthesis):
   5'TTTTGCGGCCGCGGATCCACCACCTCCCCCTCCCCCCCCC
   CCTCCTCCCCCCCCCCCCCCACCACCCCCACCCCCACC3'-OH
VI. Anti-Poly-Glycine & 3' Sites (for cDNA synthesis and PCR):
   5'TTTTGCGGCCGCGGATCCACCACCTCCC3'-OH

---

Sequences I and II are mixed in equimolar amounts in standard TE Buffer and heated at 65° C. for 5–10 min. The complementary sequences (which comprise the 5' untranslated region) are allowed to anneal at 50°–60° C. for one hour or longer, are allowed to cool slowly to room temperature, and are thereafter stored at 0°–4° C. Sequences IV and V are likewise treated to form the double-stranded 3' region. These duplexes each have an eight-base, single-stranded overhanging sequence which is complementary to the known ends of Sequence III.

Equimolar amounts of I/II duplex, IV/V duplex, and semi-random Sequence III are ligated with T4 DNA ligase overnight at 13°–15° C. in Ligase Buffer. The ligation mix is then run on a 1.5% agarose gel to separate out the desired ligation product, which is approximately 200 base pairs (233 bp if completely double-stranded, which it is not). The "200 bp" DNA band is gel purified with NA45 paper (S&S) or by any of several protocols. A total of 2.5 μg (representing approximately $10^{13}$ DNA molecules) or more is desirable.

Complete double-stranded synthesis of novel genes is accomplished with DNA Polymerase I, Klenow, using standard methods. The double-stranded 3' region provides a primer for the "second-strand" synthesis of the semi-random sequences. T4 DNA ligase is used to join the newly synthesized DNA to Sequence II, thereby filling the nick in the second strand. The DNA library is phenol/chloroform extracted and ethanol precipitated.

10 µg of completely double-stranded DNA molecules has a sequence diversity of $4 \times 10^{13}$. This library may then be transcribed with T7 RNA Polymerase to yield translatable mRNAs. However, with each transcription, the DNA library is consumed, unless DNA copies are made. To replicate the DNA library, 100 ng aliquots are each distributed to 500-µl tubes for PCR amplification in 200-µl reactions. According to *PCR Technology*, pp. 18–19 (Erlich, ibid., 1989), each 200-µl PCR reaction yields about 5.2 µg of DNA—or an approximately 50-fold duplication of DNA in each aliquot. The aliquots are pooled. The pooled sample contains on the average 50 copies of each semi-random sequence and therefore may be used repeatedly (50 times, for example) without a large loss of diversity for each translation with T7 RNA Polymerase. If the library is to be replicated with PCR, then the Klenow filling and ligation steps, described above, may be unnecessary, since the Taq polymerase is capable of filling in the gap and nick-translating DNA (D. H. Gelfand, PCR Workshop, Society of Industrial Microbiology Meeting, Seattle, Wash., 1989). After nick translation, the gene is double-stranded and able to be PCR amplified.

Examples of oligonucleotide primers for PCR amplification of the DNA library are listed above in sequences I and VI. Generally, oligonucleotides of 25–30 bases are used for PCR amplification; however, longer primers may be used. It is important that the primers do not share significant homologies or complementary 3' ends. Sequences I and VI have noncomplementary ends and no obvious regions of extensive homology.

In addition, after translation of these novel gene sequences, the resulting mRNAs lack T7 promoter sequences. Sequence VI is used as the primer for first-strand cDNA synthesis. Sequence I is used as the primer for second-strand synthesis and restores the T7 promoter to the cDNA. In this way, later rounds of translation are possible on the selected novel gene sequences. PCR amplification may be necessary if the resulting cDNAs are relatively rare.

Example 2

TRANSCRIPTION OF NOVEL GENES

The DNA library (or a representative aliquot of those sequences) described in Example One is transcribed with T7 RNA polymerase. 2.5 µg of this DNA codes for nearly $10^{13}$ different polypeptides. The DNA is capped during transcription with Stratagene's mCAP™ Kit, according to the manufacturer's specifications. Approximately 5–10 µg of mRNA is expected. Generally, with T7 RNA polymerase, nearly 10 times this level of RNA is synthesized; however, the conditions for the capping reaction limit mRNA production in this case. The DNA is removed with DNase I, provided in the kit. The capped mRNA is phenol/chloroform extracted and precipitated with ethanol. The RNA is resuspended in 10 µl of TE and stored at 0°–4° C.

Example 3

TRANSLATION OF NOVEL GENES

The capped mRNA is translated with Boehringer Mannheim Biochemical's rabbit reticulocyte kit, with all 20 amino acids at 312.5 µmol/l each. Capped mRNA from Example 2 is added to each reaction at 0.5 µg per reaction and is treated according to the manufacturer's protocol. After around 60 minutes at 30° C., cycloheximide is added to a final concentration of 1 µg/ml. $MgCl_2$ is. adjusted to 5 mM, and heparin is added to 0.2 mg/ml. The reactions are pooled and submitted to a discontinuous sucrose gradient, according to Lynch (ibid., 1987). The polysomes may be frozen at –70° C. or used directly.

Example 4

IMMOBILIZATION OF ANTIBODIES AS THE SUBSTANCE OF INTEREST

Antibodies may be used to select for novel binding peptides. Peptides which bind to the hypervariable/variable regions of the antibodies ("anti-id peptides") may behave like the original epitopes which were used as immunogens. Because the novel anti-id peptides may mimic the original epitopes, these peptides may be useful as vaccines and/or may demonstrate biological activities, in much the same way that anti-id antibodies have been shown to have biological (sometimes catalytic) activities.

Examples of useful antibodies are anti-fibronectin, anti-nerve growth factor, anti-CD4, and anti-tumor necrosis factor, which are all available from Boehringer Mannheim Biochemicals. In general, antibodies to receptor molecules, growth factors, surface antigens, and biologically active peptides, as well as neutralizing antibodies to toxins and diseases, are good candidates for which to isolate anti-id binding peptides that may have agonist or antagonist properties or serve as vaccines.

The antibodies are affixed to Immobilon™ PVDF (polyvinylidene difluoride) membrane from Millipore Corporation, according to Pluskal et al. (*BioTechniques* 4:272–283, 1986). For example, anti-fibronectin antibody (from clone 3E3, Boehringer Mannheim Biochemicals) is absorbed onto a 0.5 cm×0.5 cm square of PVDF, that has been "wetted" with 100% methanol and washed twice with 0.9% (w/v) NaCl in 10 mM Tris buffer pH 7.4 (Saline Buffer). The amount of antibody needed is dependent upon the binding parameters of the desired anti-id peptides(s); Immobilon™ PVDF is reported to bind 172 µg/cm² of IgG. For convenience, 1 µg of anti-fibronectin $IgG_1$ in saline buffer is absorbed onto the PVDF square by incubating at room temperature for at least two hours. The PVDF is then washed with the Saline Buffer twice. The membrane is next incubated with a "blocking solution," containing 5% (w/v) gelatin in saline buffer for at least two hours at room temperature, so that the gelatin is absorbed into unoccupied sites of the PVDF. The membrane is then washed twice with 0.1% gelatin in saline buffer. A similar treatment is done with 10 µg anti-keratin antibody (from clone AE1, Boehringer Mannheim Biochemicals), which is the control $IgG_1$ as described below.

Example 5

POLYSOME BINDING TO ANTIBODIES

Polysomes with nascent semi-random peptides are incubated in 1-ml reactions, each containing PS Buffer (0.9% NaCl, 10 mM Tris pH 7.4, 1% gelatin, 15 mM $MgCl_2$, 0.2 mg/ml heparin, and 1 µg/ml cycloheximide) and a PVDF square with 10 µg anti-keratin $IgG_1$, described in Example 4. This pre-absorption step is done at 0°–4° C. with gentle agitation for four hours to select out nonspecific binding of polysomes to gelatin and $IgG_1$. The anti-keratin PVDF square is removed with jewelers' forceps and is replaced with the anti-fibronectin PVDF square. The mixture is incubated for four more hours under the same conditions to allow specific polysome binding to the variable/hypervariable region of the anti-fibronectin antibody. The anti-fibronectin PVDF square is removed and washed three times by transferring it serially to fresh PS buffer.

Example 6

RECOVERING NOVEL GENES WHICH CODE FOR ANTI-ID PEPTIDES FROM POLYSOMES

The PVDF membrane, which holds the washed antibody-bound polysomes, is transferred to a tube containing 100 µl of 0.1 mM EDTA and is gently shaken at room temperature for 5–10 minutes to disrupt the polysomes and liberate mRNA. The PVDF is removed, placed in a fresh tube of 0.1 mM EDTA, and stored at 0°–4° C. overnight or longer (as a back-up). The released mRNA from the first EDTA treatment is reverse transcribed; and the resulting cDNA is amplified, according to PCR Technology (ibid., 1989), p. 91, with slight modification. Instead of using random hexamer for priming the cDNA synthesis, a sequence complementary with the known 3' region (such as Sequence VI listed earlier as the downstream primer) is used for both cDNA synthesis and PCR reactions. The reverse transcriptase step is done in 100 µl of PCR buffer with the appropriate relative amounts of the other reagents (instead of 20-µl reaction). After the reverse transcriptase reaction, the mixture is split into 20 µl aliquots; and each aliquot is amplified as described in this book, using Sequence I or a similar DNA upstream primer. After PCR amplification, the five aliquots are pooled, phenol/chloroform extracted, and ethanol precipitated. This cDNA is then resuspended in TE and stored at 0°–4° C.

The selected DNA is transcribed with T7 RNA polymerase and translated in a reticulocyte system, as previously described. In this case, the desired sequences are greatly amplified compared to the original DNA library. By repetition of this cycle, which is greatly aided through the use of programmable workstations, desirable novel genes are concentrated to a level where conventional cloning and expression methods are practical. In addition, by dilution to low Poisson Distribution of genes, a single novel gene(s) may be isolated, amplified, transcribed, and translated to demonstrate specific binding capability of the gene product(s). Once binding has been demonstrated, the isolated gene(s) and polypeptide(s) may be sequenced for identification.

After the sequence of the novel binding peptide is known, many methods exist for the manipulation and large-scale synthesis of the peptide, as described in the specification.

From the foregoing it will be appreciated that, although specific embodiments of the invention have been described herein for the purposes of illustration, various modifications may be made without deviations from the spirit and scope of the invention. Accordingly, the invention is not to be limited except as by the following claims.

We claim:

1. A method for producing novel polypeptides, comprising:
    (a) constructing an in vitro expression unit comprising a 5' untranslated region containing an RNA polymerase binding site, a ribosome binding site, and a translation initiation signal, said expression unit being capable of producing mRNA;
    (b) attaching one or more semi-random polynucleotides to said expression unit;
    (c) transcribing or replicating from the RNA polymerase binding site the polynucleotides associated with the expression unit and semi-random polynucleotides to produce mRNA;
    (d) translating said mRNA to produce polysomes under conditions sufficient to maintain said polysomes;
    (e) binding said polysomes to a substance of interest;
    (f) isolating said polysomes that bind to said substance of interest;
    (g) disrupting said isolated polysomes to release mRNA;
    (h) recovering said mRNA;
    (i) constructing cDNA from said recovered mRNA; and
    (j) expressing said cDNA to produce novel polypeptides.

2. The method of claim 1 wherein, after the step of constructing the cDNA, the cDNA is amplified by polymerase chain reaction.

3. The method of claim 1 wherein said semi-random polynucleotide comprises deoxyribonucleic acid.

4. The method of claim 1 wherein said semi-random polynucleotide comprises ribonucleic acid.

5. The method of claim 1 wherein the RNA polymerase binding site is a RNA-directed RNA polymerase binding site.

6. The method of claim 5 wherein said RNA-directed RNA polymerase is Q-Beta replicase.

7. The method of claim 1 wherein, subsequent to the step of recovering, amplifying the mRNA.

8. The method of claim 7 wherein the step of amplifying comprises synthesizing polynucleotide with an RNA-dependent RNA polymerase.

9. The method of claim 8 wherein the RNA-dependent RNA polymerase is Q-Beta replicase.

10. The method of claim 1 wherein the step of isolating comprises removing polysomes that do not bind to said substance of interest by serial dilution or flow-through wash steps.

11. The method of claim 1 wherein, subsequent to the step of isolating said polysomes, said polysomes are exposed to selected stringency conditions such that said polysomes are released from said substance of interest.

12. The method of claim 11 wherein the step of exposing said polysomes comprises raising the temperature, lowering the salt concentration, or raising the metal ion concentration of said polysomes.

13. A method for producing novel polypeptides, comprising:
    (a) constructing an in vitro expression unit comprising a 5' untranslated region containing an RNA polymerase binding site, a ribosome binding site, and a translation initiation signal, said expression unit being capable of producing mRNA;
    (b) attaching one or more semi-random polynucleotides to the expression unit;
    (c) transcribing from the RNA polymerase binding site the polynucleotides associated with the expression unit and semi-random polynucleotides to produce mRNA;
    (d) translating said mRNA in vitro to produce biologically active polypeptides;
    (e) subdividing the mRNA encoding said biologically active polypeptides;
    (f) transcribing, translating, and subdividing as set forth in steps (c)–(e), such that the gene of interest is isolated;
    (g) constructing cDNA from said isolated gene; and
    (h) expressing said cDNA to produce novel polypeptides.

14. A method for producing novel polypeptides, comprising:

(a) constructing an in vitro expression unit comprising a 5' untranslated region containing an RNA polymerase binding site, a ribosome binding site, and a translation initiation signal, said expression unit being capable of producing mRNA;

(b) attaching one or more semi-random polynucleotides to the expression unit;

(c) replicating from the RNA polymerase binding site the polynucleotides associated with the expression unit and semi-random polynucleotides to produce mRNA;

(d) translating said mRNA in vitro to produce biologically active polypeptides;

(e) subdividing the mRNA encoding said biologically active polypeptides;

(f) translating and subdividing as set forth in steps (d)–(e) such that the gene of interest is isolated;

(g) constructing cDNA from said isolated gene; and (h) expressing said cDNA to produce novel polypeptides.

15. The method of claim 13 wherein, subsequent to the step of subdividing the RNA, amplifying the novel polynucleotides encoding the biologically active polypeptides with polymerase chain reaction or with an RNA-directed RNA polymerase.

16. The method of claims 1, 13 or 14 wherein said ribosome binding site is a prokaryotic ribosome binding site.

17. The method of claims 1, 13 or 14 wherein said ribosome binding site is a viral ribosome binding site.

18. The method of claims 1, 13 or 14 wherein said ribosome binding site is a eukaryotic ribosome binding site.

19. The method of claims 1, 13 or 14 wherein said ribosome binding site comprises the vertebrate consensus translation initiation sequence GCCGCCACCATGG, or functionally equivalent polynucleotides.

20. The method of claims 1, 13 or 14 wherein the expression unit further comprises a polynucleotide which codes for a selected amino-terminal ID peptide, said polynucleotide positioned at the 3' end of the initiation codon.

21. The method of claim 1, 13 or 14 wherein the expression unit further comprises a 3' region of a selected polynucleotide, said selected polynucleotide selected from the group consisting of polynucleotides enhancing the amplification, cloning, replication, purification, and isolation of the novel genes.

22. The method of claim 21 wherein the 3' region includes palindromic polynucleotides to impede ribosome translocation.

23. The method of claim 21 wherein said 3' region includes a C-terminal polynucleotide which codes for an ID peptide.

24. The method of claim 23 wherein the C-terminal polynucleotide coding for an ID peptide comprises a repetitive sequence.

25. The method of claim 23 wherein the C-terminal polynucleotide codes for a peptide capable of binding to antibodies.

26. The method of claim 1, 13 or 14 wherein the expression unit further comprises restriction sites to allow expression of the novel gene in vivo.

27. The method of claim 26 wherein at least one of said restriction sites comprises the sequence CCATGG, said site positioned at the start of translation.

28. The method of claim 1, 13 or 14 wherein the 5' untranslated region of said expression unit includes the promoter for T7, T3, or SP6 polymerase in the 5' untranslated region.

29. The method of claim 1, 13 or 14 wherein the semi-random polynucleotides are generated by mechanically, chemically, or enzymatically fragmenting naturally-occurring DNA or cDNA.

30. The method of claim 1, 13 or 14 wherein the semi-random polynucleotides are generated by chemically synthesizing polynucleotides to form gene sequences.

31. The method of claim 30 wherein the step of synthetically synthesizing said nucleotides comprises the steps of (1) utilizing substantially equal molar amounts of C, A, and G, and only half of said substantially equal molar amount of T in the first codon positions; (2) utilizing substantially equal molar amounts of C, T, and G, and only half of said substantially equal molar amount of A in the second codon positions; and (3) utilizing substantially equal molar amounts of only C and G in the third codon positions.

32. The method of claim 1, 13 or 14 wherein the step of attaching further comprises polymerizing said nucleotides directly onto the 3' end of the 5' untranslated region of the expression unit.

33. The method of claim 1 or 13 wherein the step of transcribing comprises transcribing said polynucleotides in the presence of diguanosine triphosphate or analogs thereof.

34. The method of claim 1, 13 or 14 wherein the step of translating comprises translating said polynucleotides in the presence of diguanosine triphosphate or analogs thereof and guanylyltransferase.

35. The method of claim 1, 13 or 14 wherein the step of translating is conducted in the presence of nonsense-suppressing tRNAs.

36. The method of claim 35 wherein the nonsense-suppressing tRNA is a tyrosine-inserting, nonsense-suppressing tRNA.

37. The method of claim 1, 13 or 14 wherein said substance of interest is selected from a group consisting of surface antigens, receptor proteins, toxins, organic polymers, metabolites, active sites of protein molecules, hormones, antibodies, and pollutants.

38. The method of claim 1, 13 or 14 wherein said substance of interest is the variable/hypervariable region of an antibody.

39. The method of claim 1, 13 or 14 wherein said substance of interest is a receptor protein.

40. The method of claim 39 wherein said receptor protein is a growth factor receptor protein.

41. The method of claim 40 wherein said growth factor receptor protein is selected from the group consisting of insulin and epidermal growth factor.

42. The method of claim 1, 13 or 14 wherein said substance of interest is selected from the group consisting of viral surface antigen, viral receptor protein and CD4.

43. The method of claim 1, 13 or 14 wherein the step of expressing cDNA comprises chemically synthesizing the peptide encoded by said cDNA.

44. The method of claim 1, 13 or 14 wherein the step of expressing cDNA comprises cloning the polynucleotide into an expression vector for polypeptide synthesis in genetically engineered microorganisms.

45. The method of claim 1, 13 or 14 wherein the step of expressing cDNA comprises in vitro transcription and/or translation of the polynucleotide.

46. The method of claim 1, 13 or 14 wherein the step of expressing cDNA comprises synthesizing a polynucleotide encoding a polypeptide substantially homologous to that encoded by said cDNA, the polypeptide encoded by said polynucleotide being substantially identical to the binding region of said polysomes that bind to the substance of interest.

47. The method of claim 1, 13 or 14 wherein said cDNA is joined to other selected polynucleotides selected from the group consisting of polynucleotides encoding toxins, antibodies, enzymes, biologically active peptides, and peptides capable of binding to antibodies.

48. A method for producing novel polypeptides, comprising:
   (a) constructing an in vitro expression unit comprising a 5' untranslated region containing an RNA polymerase binding site, a ribosome binding site, and a translation initiation signal, said expression unit being capable of producing mRNA;
   (b) attaching one or more semi-random polynucleotides to said expression unit adjacent to a polynucleotide sequence encoding a fixed amino acid sequence;
   (c) transcribing or replicating from the RNA polymerase binding site the polynucleotides associated with the expression unit and semi-random polynucleotides to produce mRNA which encodes a polypeptide of at least about fifty amino acids;
   (d) translating said mRNA to produce polysomes under conditions sufficient to maintain said polysomes;
   (e) binding said polysomes to a substance of interest;
   (f) isolating said polysomes that bind to said substance of interest;
   (g) disrupting said isolated polysomes to release mRNA;
   (h) recovering said mRNA;
   (i) constructing cDNA from said recovered mRNA; and
   (j) expressing said cDNA to produce novel polypeptides.

49. The method of claim 48, wherein the semi-random polynucleotides encode a peptide of about 30 amino acids.

50. The method of claim 48, wherein the polynucleotide sequence encoding a fixed amino acid sequence encodes an amino acid sequence of at least 20 amino acids.

* * * * *